US005678543A

United States Patent [19]

Bower

[11] Patent Number: 5,678,543

[45] Date of Patent: Oct. 21, 1997

[54] HYPERBARIC CHAMBER

[75] Inventor: James W. Bower, Ilion, N.Y.

[73] Assignee: Portable Hyperbarics, Inc., Ilion, N.Y.

[21] Appl. No.: 558,707

[22] Filed: Nov. 16, 1995

[51] Int. Cl.[6] .................................................. A61M 11/00

[52] U.S. Cl. ................................ 128/205.26; 128/202.12

[58] Field of Search ......................... 128/200.24, 202.12, 128/204.18; D24/164; 600/21, 22; 52/2.17

[56] References Cited

U.S. PATENT DOCUMENTS

| | | | |
|---|---|---|---|
| 3,602,221 | 8/1971 | Bleicken | 128/205.26 |
| 3,729,002 | 4/1973 | Miller | 128/205.26 |
| 4,196,656 | 4/1980 | Wallace et al. . | |
| 4,509,513 | 4/1985 | Lasley | 128/205.26 |
| 4,974,829 | 12/1990 | Gamow et al. . | |

OTHER PUBLICATIONS

Open Water Sport Diver Manual, Jeppesen Sanderson, Inc. 1989.

*Primary Examiner*—V. Millin
*Assistant Examiner*—Robert R. Wieland
*Attorney, Agent, or Firm*—Donald W. Huntley

[57] ABSTRACT

Lightweight hyperbaric chamber capable of maintaining pressures of up to 22 psi greater than ambient through the use of at least two zippers, at least one of which is a sealing zipper, and preferably with heavy fabric and a reinforcing outer layer.

14 Claims, 2 Drawing Sheets

HYPERBARIC CHAMBER

BACKGROUND OF THE INVENTION

Athletic activities such as mountain climbing and skiing take humans to high altitudes and subject them to reduced ambient pressure. Such reduced atmospheric pressures can lead to what is commonly known as mountain sickness. Symptoms of mild mountain sickness include nausea and headache, which can go away after a few days. In some cases, it may be desirable to transport the sick person to higher atmospheric pressures. However, this is not always possible, and hyperbaric chambers have previously been developed to provide a quick, efficient and effective way of treating patients that are affected by mountain sickness.

Historically hyperbaric chambers have been heavy, rigid structures, such as that described in Wallace et al., U.S. Pat. No. 4,196,656. That patent discloses hyperbaric chambers with cylindrical shapes, large enough to admit human beings and allow movement within the chamber. More recently, Gamow et al., in U.S. Pat. No. 4,974,829, disclosed a portable hyperbaric chamber for use at higher elevations. The Gamow hyperbaric chamber can be used by climbers suffering from mountain sicknesses, and provides a hyperbaric chamber that can achieve and maintain air pressure inside the chamber from 0.2 psi to 10 psi greater than ambient. However, there are times when air pressure higher than 10 psi greater than ambient is necessary, for example, for decompression sickness, burn therapy, treatment of $CO_2$ poisoning, and other illnesses and injuries.

SUMMARY OF THE INVENTION

The hyperbaric chambers of the present invention can achieve internal pressures that are significantly higher than prior hyperbaric chambers, while retaining a high degree of portability.

Specifically, the present invention provides, in a lightweight, portable, inflatable and collapsible hyperbaric chamber, with sides made of flexible, foldable and non-breathable material, the sides having an outer surface, the chamber having a pressurizing means and a differential pressure valve outlet means for achieving a desired air pressure inside the chamber, and means for ingress and egress which can be closed to prevent loss of pressurized air, the improvement wherein the pressurizing means and the differential valve outlet means can achieve and maintain air pressure inside the chamber within the range of about from 0.2 to 22 psi greater than ambient, and the means for ingress and egress comprises at least one inner layer and at least one outer layer, each layer having a zipper closure, and wherein at least one of the zippers is a sealing zipper.

The instant hyperbaric chambers are optionally provided with a reinforcing outer layer, which is positioned externally adjacent to the outer surface of the hyperbaric chamber such that it at least partially envelops the outer surface of the chamber. The reinforcing outer layer is preferably a fabric that weighs at least about 20 oz/sq.yd.

BRIEF DESCRIPTION OF THE INVENTION

DETAILED DESCRIPTION OF THE INVENTION

Figure 1:
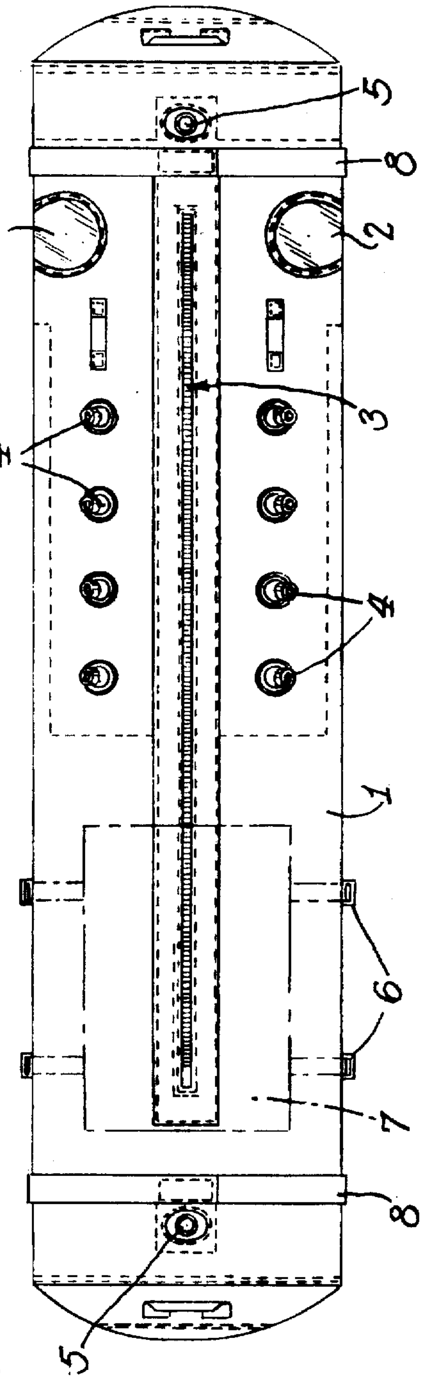
FIG. 1 is a top plan of a hyperbaric chamber of the present invention.
Figure 2:
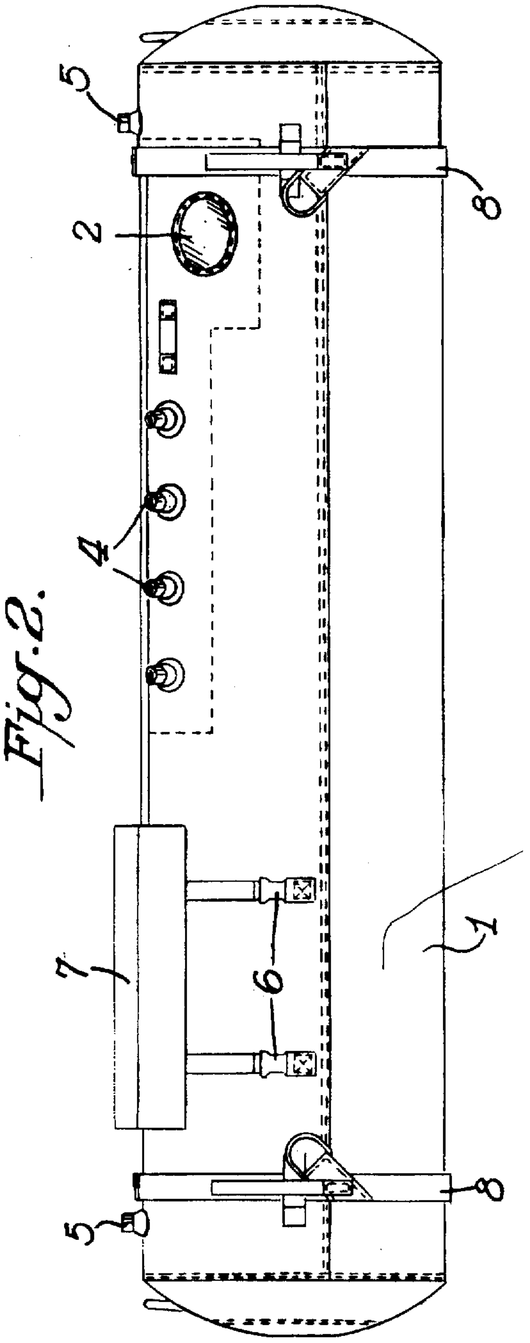
FIG. 2 is a side view of the hyperbaric chamber of FIG. 1.
Figure 3:
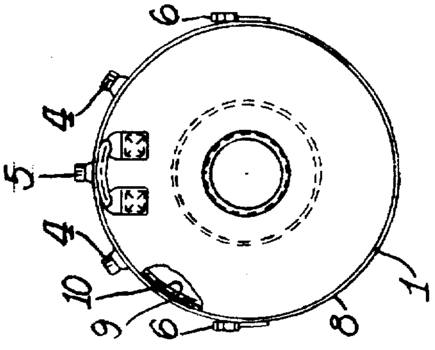
FIG. 3 is an end view of the hyperbaric chamber of FIG. 2, partly broken away to show the layers of the wall construction.

The invention will be more fully understood by reference to the drawings, in which FIG. 1 is an exterior view of a hyperbaric chamber, having exterior wall 1, windows 2 constructed of clear material, a means for ingress and egress 3 that can be either a sealing or mechanical zipper and means, not shown, connected to the interior of the hyperbaric chamber via ports 4. The choice of particular pressurizing means can vary widely among available means of air compression, including, for example, mechanical compressors or supplies of compressed air or oxygen. Pressure valves 5 can adjust or maintain a predetermined internal pressure. Mounting means 6 are provided for a saddle 7 for a compressed air tank, as shown in FIG. 2. The external walls are shown with optional reinforcing bands 8. FIG. 3 is an end view of the chamber, partly broken away to show the layers of the wall construction. As shown there, the hyperbaric chamber is constructed with a non-breathable material 9 and a reinforcing fabric layer 10 which is shown here to fully envelop the outer surface of the chamber. A means for ingress and egress 3 can be closed by using either a sealing or a mechanical zipper, with the proviso that at least one of the zippers is a sealing zipper. The length of the hyperbaric chamber is typically about 80 inches and the circumference is typically about 74 inches.

Figure 4:
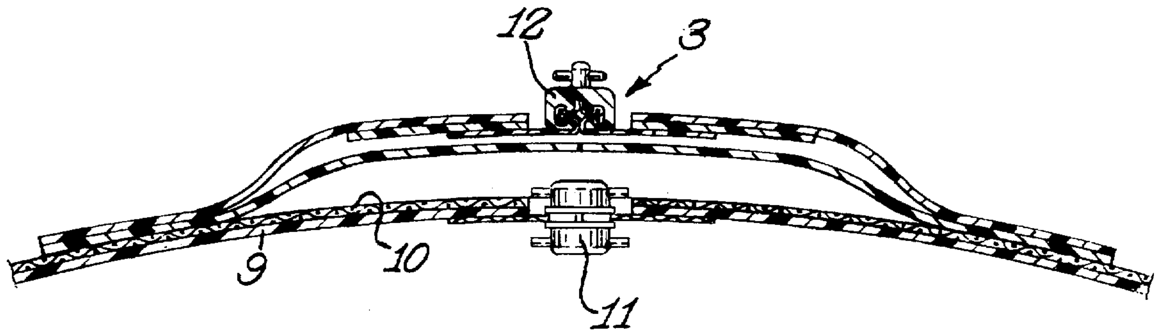
FIG. 4 is a cross-sectional view of a representative closure in a preferred embodiment of the present invention, having a reinforcing layer.

FIG. 4 details the construction of a preferred embodiment of the present invention having reinforcing fabric layer 10. The means for ingress and egress of the hyperbaric chamber, generally indicated as 3, is equipped with a combination of an air permeable mechanical zipper 11 and an air impermeable sealing zipper 12. The reinforcing fabric layer is equipped with a mechanical zipper 13. This combination of zippers ensures that the internal pressure of the hyperbaric chamber is maintained as desired. A combination of at least one sealing zipper and a second zipper ensures the maintenance of the desired elevated pressures within the chamber. The second zipper, whether it is a mechanical zipper or a sealing zipper, permits at least one sealing zipper to maintain its integrity with the elevated temperature and motion of the hyperbaric chamber.

The particular mechanical and sealing zippers used can be selected from those commercially available for both purposes. In general, the mechanical zipper should have a crosswise strength of at least about 300 pounds. Sealing zippers of the types used for underwater wet and dry suits and available from Talon Corporation, Dynat or YKK can be used in the present constructions. Particularly satisfactory zippers are those commercially available as the Talon 1731 sealing zipper and the Talon 1880 mechanical zipper.

The flexible, foldable and non-breathable material used for the basic construction of the present chambers can vary widely, and preferably has a weight of at least about 20 oz./yd. In general, the material is woven or knitted, preferably has a weight of about from 20 to 30 oz./yd., and is typically prepared from polymeric materials such as polyamides and polyesters. Typical polyamides which can be used include nylon 6 and nylon 66, as well as nylon 610 and nylon 612. Polyesters which can be used include, for example, polyethylene terephthalate and polybutylene terephthalate. Filaments of at least about 800 denier are preferred.

To improve the impermeability of the fabric used for construction of the chamber, it is preferably coated with a polymeric material, such as polyurethane or vinyl.

The reinforcing outer layer, or girdle, can be prepared from the same materials as the chamber itself. However, since the outer layer performs only a reinforcing function, further sealing with a polymeric coating is unnecessary. In general, the reinforcing layer, when used, will envelope at least about 40% of the exterior surface area of the chamber.

The means for ingress and egress in the reinforcing layer are substantially parallel to the ingress and egress means of the hyperbaric chamber itself, the means for ingress and egress of the hyperbaric chamber and the reinforcing outer layer, taken collectively, have at least one sealing zipper.

In a preferred embodiment of the present invention, $CO_2$ absorption means is disposed on the interior of the chamber to permit maximum utilization of the available oxygen within the chamber. A wide variety of carbon dioxide absorption means can be used in the present invention, including, for example, alkali metal hydroxides and oxides, and sodium carbonate. Of these, the lithium and sodium salts are preferred, and lithium hydroxide in particulate form is particularly preferred. In addition, $CO_2$ absorbents in liquid or gel form can be used.

The $CO_2$ removal means, when used, is generally encased in semi-permeable membrane. The membrane preferably has a number average pore size of about from 10 to 10 microns. This pore size permits contact of the gas and moisture within the chamber and the $CO_2$ removal means, but prevents the smaller particles of $CO_2$ removal means from escaping into the breathing portion of the chamber. The $CO_2$ absorption means is disposed on the interior of the chamber, so as to bring the $CO_2$ removal means in contact with the gas within the chamber.

The $CO_2$ absorbent can be disposed on the interior of the chamber by any convenient means, including, for example, adhesive bonding to the sidewalls. However, regardless of the particular method of attaching the $CO_2$ absorption means to the interior walls of the chamber, the $CO_2$ absorption means should be covered by a semi-permeable membrane which simultaneously prevents direct inhalation of dust from the $CO_2$ adsorption means while permitting contact with the gas inside the chamber.

We claim:

1. In a lightweight, portable, inflatable and collapsible hyperbaric chamber, with sides made of flexible, foldable and non-breathable material, the sides having an outer surface, the chamber having a pressurizing means and a differential pressure valve outlet means for achieving and maintaining air pressure inside the chamber, and means for ingress and egress which can be closed to prevent loss of pressurized air, the improvement wherein the pressurizing means and the differential pressure valve outlet means can achieve air pressure inside the chamber within the range of about from 0.2 to 22 psi greater than ambient, and the means for ingress and egress comprises at least one inner layer and at least one outer layer, each layer having a zipper closure and wherein one of the zippers is a mechanical zipper.

2. A hyperbaric chamber of claim 1 wherein the sealing zipper is located on an inner layer and the mechanical zipper is located on an outer layer.

3. A hyperbaric chamber of claim 1 wherein the mechanical zipper is located on the inner layer and the sealing zipper is located on the outer layer.

4. A hyperbaric chamber of claim 1 wherein the flexible, foldable and non-breathable material weighs at least about 20 oz./sq.yd.

5. A hyperbaric chamber of claim 4 wherein the flexible, foldable and non-breathable material has a weight of about from 20 to 30 oz./sq. yd.

6. A hyperbaric chamber of claim 1 wherein the chamber further comprises a reinforcing outer layer positioned externally adjacent to the outer surface of the hyperbaric chamber, such that it at least partially envelops the outer surface of the sides, and having a means for ingress and egress; and wherein the means of ingress and egress of the reinforcing layer is substantially aligned with the means for ingress and egress of the hyperbaric chamber.

7. A hyperbaric chamber of claim 6 wherein the flexible, foldable and non-breathable material weighs at least about 20 oz./sq. yd.

8. A hyperbaric chamber of claim 7 wherein flexible, foldable and non-breathable material is a synthetic fabric and consists essentially of at least one polymer selected from polyesters and polyamides.

9. A hyperbaric chamber of claim 8 wherein the reinforcing layer consists essentially of nylon fabric.

10. A hyperbaric chamber of claim 9 wherein the nylon fabric consists essentially of nylon 66.

11. A hyperbaric chamber of claim 9 wherein the nylon material of the reinforcing layer comprises filaments of at least about 800 denier.

12. A hyperbaric chamber of claim 10 wherein the nylon material of the reinforcing layer comprises filaments of at least about 800 denier.

13. A hyperbaric chamber of claim 9 wherein the nylon fabric of the reinforcing layer has a weight of at least about 20 oz/sq. yd.

14. A hyperbaric chamber of claim 6 wherein the means for ingress and egress in the reinforcing layer comprises a mechanical zipper.

* * * * *